United States Patent [19]
Cameron et al.

[11] Patent Number: 5,733,749
[45] Date of Patent: Mar. 31, 1998

[54] GLYCEROL PHOSPHATASE WITH STEREO-SPECIFIC ACTIVITY

[75] Inventors: Douglas C. Cameron; Frank A. Skraly, both of Madison, Wis.

[73] Assignee: Wisconsin Alumni Research Foundation, Madison, Wis.

[21] Appl. No.: 514,579

[22] Filed: Aug. 14, 1995

[51] Int. Cl.$^6$ .......................... C12P 19/00; C07C 31/22; C12N 1/20; C07H 21/04
[52] U.S. Cl. .................. 435/72; 435/252.3; 435/252.31; 435/252.5; 435/274; 435/280; 435/836; 536/23.2
[58] Field of Search ..................... 435/72, 252.3, 435/252.31, 196, 274, 280, 252.5, 836; 536/23.2

[56] References Cited

PUBLICATIONS

Baer, E., and H. O. L. Fischer, "Synthesis of the d(+)-α-Glycerophosphoric Acid and the Action of Phosphatases on Synthetic d(+)-, l(-)-, and dl-α-Glycerophosphoric Acids," *J. Biol. Chem.* 135: 321–328 (1940).

Ball, E. G. (ed.), *Biochemical Preparations,* John Wiley & Sons, New York, 1952, pp. 31–38.

Belmans, D., and A. Van Laere, "Glycerol-3-Phosphatase and the Control of Glycerol Metabolism in *Dunaliella tertiolecta* Cells," *Arch. Microbiol.* 150: 109–112 (1988).

Gancedo, C., et al., "Glycerol Metabolism in Yeasts: Pathways of Utilization and Production," *European J. Biochem.* 5: 165–172 (1968).

Roberts, S. M. et al., (eds), *Introduction to Biocatalysis Using Enzymes and Micro-Organisms,* Cambridge University Press, 1995, pp. 132–139.

Schomburg, D. and M. Salzmann, *Enzyme Handbook* 3, Springer-Verlag, Berlin, 1991, EC 3.1.2.21, pp. 1–4.

Sussman, I., and M. Avron, "Characterization and Partial Purification of DL-Glycerol-1-Phosphatase from *Dunaliella salina,*" *Biochimica et Biophysica Acta* 661: 199–204 (1981).

Van Schaftingen, and A. J. Van Laere, "Glycerol Formation After the Breaking of Dormancy of *Phycomyces blakesleeanus* Spores," *Eur. J. Biochem.* 148: 399–404 (1985).

Primary Examiner—Robert A. Wax
Assistant Examiner—Elizabeth Slobodyansky
Attorney, Agent, or Firm—Quarles & Brady

[57] ABSTRACT

A biologically pure enzyme comprising D-α-glycerophosphatase from *Bacillus licheniformis* is disclosed. A genetic construction in a heterologous host capable of producing D-α-glycerophosphate is also disclosed, wherein the construction includes a protein coding sequence for D-α-glycerophosphatase from *Bacillus licheniformis*.

11 Claims, 3 Drawing Sheets

GLYCEROL PHOSPHATASE WITH STEREO-SPECIFIC ACTIVITY

FIELD OF THE INVENTION

The present invention is directed to a glycerol phosphatase capable of converting D-α-glycerophosphate to glycerol.

BACKGROUND OF THE INVENTION

As part of their normal metabolism, many microbes oxidize sugars to form various compounds in the absence of respiration. Examples of the resulting microbial products include the primary metabolites, which must be formed to dispose of catabolically generated reducing equivalents.

One important example of such a metabolite is glycerol, long known to be a minor byproduct of the fermentation of glucose to ethanol in organisms used for alcoholic beverage production, such as *Saccharomyces cerevisiae*. Pasteur, L., C. R. Hebd. Seances Aca. Sci. 46:857, 1858. Many osmotolerant yeasts and algae produce glycerol and other polyols as major products from sugars as a defense mechanism against hypertonic surroundings. A few species of bacteria are known to ferment sugars to glycerol: *Lactobacillus lycopersici* (*L. buchneri*) and *Lactobacillus acidophilaerogenes* (*L. plantarum*), Nelson, et al., J. Bacteriol. 30(6):547–557, 1935, *Zymomonas mobilis*, Horbach et al., FEMS Microbiol. Lett., 120:37–44, 1994, and at least one strain of *Bacillus licheniformis*. Neish, A. C. et al., Can. J. Res. 23, Pt.B:290–296, 1945.

Glycerol is not only a primary metabolite in the fermentation of sugars in many organisms, but also a fermentable substrate for others. Examples of valuable glycerol-derived fermentation products include 3-hydroxypropionaldehyde, 1,3-propanediol, 3-hydroxypropionic acid, dihydroxyacetone phosphate, and dihydroxyacetone. Microbes capable of fermenting glycerol to such valuable products can theoretically be genetically manipulated to enable the microbes to convert sugars to the products as well, by expressing in the microbe genes able to confer the ability to convert sugars to glycerol. The ability of such genetically manipulated organisms to use less expensive substrates such as fermentable sugars could reduce the cost of industrial fermentations.

One such glycerol production enzyme is L(or D)-α-glycerophosphatase, which dephosphorylates L(or D)-α-glycerophosphate (a precursor of phospholipid synthesis) to produce glycerol. Theoretically, once a glycerophosphatase is isolated and purified, the gene encoding the enzyme could be transformed into any host, such as a bacterium, that produces the appropriate glycerophosphate, thereby enabling the host to form glycerol from sugars.

SUMMARY OF THE INVENTION

In one embodiment, this invention provides a biologically pure enzyme comprising a D-α-glycerophosphatase with stereo-specific activity.

In other aspects, the invention provides a biologically pure sample of DNA which includes sequence coding for the expression of D-α-glycerophosphatase from *Bacillus licheniformis*, and a vector and microbial host containing the biologically pure sample of DNA. The invention further provides a genetic construct in a heterologous host capable of producing D-α-glycerophosphate, which construct comprises a DNA sequence for the D-α-glycerophosphatase from *Bacillus licheniformis*.

In another embodiment, the invention provides a method for the production of glycerol from sugars by culturing, under conditions suitable for the expression of *Bacillus licheniformis* D-α-glycerophosphatase, a D-α-glycerophosphate-producing host transformed with a genetic construction including a coding sequence for *Bacillus licheniformis* D-α-glycerophosphatase, and recovering glycerol from the culture.

It is an object of the present invention to provide a biologically pure peptide comprising D-α-glycerophosphatase from *Bacillus licheniformis*.

It is another object of the present invention to provide a biologically pure sample of DNA which includes a sequence coding for the expression of D-α-glycerophosphatase from *Bacillus licheniformis*.

It is also an object of the present invention to provide a method of preparing glycerol and/or other products derived by fermentation of glycerol from sugars.

It is a feature of the present invention in that it enables the stereospecific purification of a racemic mixture of DL-α-glycerophosphatase to recover purified L-α-glycerophosphate, which is the conventionally biologically useful form of the molecule.

Other features and advantages of the invention will be apparent from the following description of the preferred embodiments thereof and from the claims.

DETAILED DESCRIPTION OF THE INVENTION

Figure 1A:
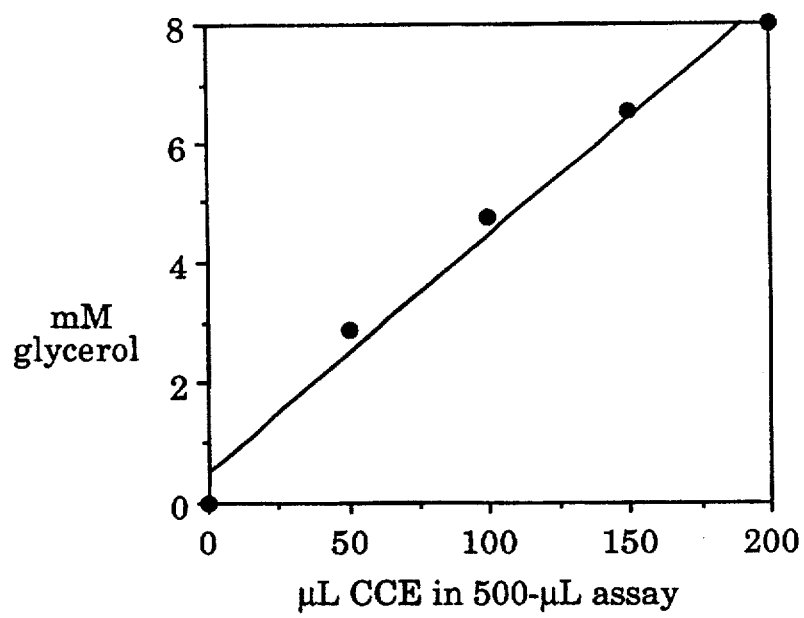
FIGS. 1a and 1b are graphs illustrating the results of the D-GPase assay, showing various levels of glycerol production.

The present invention describes the purification and characterization of a stereospecific enzyme, D-α-glycerophosphatase (abbreviated in the following discussion as "D-GPase" and which also may be referred to as sn-glycerol-1-phosphatase). D-GPase dephosphorylates D-α-glycerophosphate (abbreviated in the following discussion as "D-GP") to produce glycerol. The stereoisomer D-α-glycerophosphate is synonymous, using other nomenclature conventions, with S-glycerol-1-phosphate, D-glycerol-1-phosphate, sn-glycerol-1-phosphate, d-glycerol-3-phosphate, and (+)-glycerol-3-phosphate. D-GP is the stereoisomer of L-α-glycerophosphate (abbreviated in the following discussion as "L-GP"), which, in other conventions, is also known as R-glycerol-1-phosphate, L-glycerol-1-phosphate, sn-glycerol-3-phosphate, 1-glycerol-3-phosphate, and (−)-glycerol-3-phosphate. L-GP is the predominant stereoisomer in biological systems where it serves as a precursor of phospholipid synthesis. The enzyme L-α-glycerophosphatase (abbreviated in the following discussion as "L-GPase") dephosphorylates L-GP to produce glycerol.

The present inventors began the research leading to the present invention with the intention of purifying the enzyme L-GPase from a bacterium capable of converting glucose to glycerol. The gene encoding the enzyme's activity could then be transformed into any bacterium that produces L-GP as a precursor of phospholipid synthesis, thereby enabling the organism to form glycerol from sugars. The inventors expected that the activity would be specific for, or at least preferential for, L-GP because dephosphorylation of L-GP is the final step in glycerol synthesis in many organisms, including *Saccharomyces cerevisiae*, Gancedo, et al., Eur. J. Biochem. 5: 165–172, 1968, *Phycomyces blakesleeanus*, Van Schaftigen, et al., Eur. J. Biochem. 148: 399–405, 1985, *Dunaliella tertiolecta*, Belmans, et al., Arch. Microbiol. 150: 109–112, 1988, and *Dunaliella salina* Sussman, et al., Biochim. Biophys, Acta 661: 199–204, 1981. *Z. mobilis* was eliminated as a source of such an activity because Horbach et al. have shown that glycerol in *Z. mobilis* fructose fermentations is derived from dihydroxyacetone phosphate (DHAP) via a DHAP phosphatase and dihydroxyacetone reductase, Horbach et al., FEMS Microbiol. Lett. 120:37–44, 1994. *Z. mobilis* also forms glycerol in small amounts, and only from fructose. The inventors chose "Ford's strain" of *B. licheniformis* as the source of a pathway from glucose to glycerol because it is a robust producer of glycerol, Neish, et al., Can. J. Res. 23, Pt. B: 290–296, 1945.

Surprisingly, the inventors failed to recover L-GPase in *B. licheniformis*, but rather discovered the enzyme D-GPase, which is highly specific for D-GP, showing a clear preference for this isomer over L-GP and β-glycerophosphate (also designated β-GP and sn-glycerol-2-phosphate).

The present invention is the first known report of a specific D-GPase. All previously reported GPases have been L-GPases or DL-GPases (EC 3.1.3.21). In fact, there is some confusion in the literature regarding the stereospecificity of GPases. For example, contradictory speculations about the stereoisomer of GP from which glycerol is produced in yeast have been made. In a 1967 review of glycerol by Rehm, Industrielle Mikrobiologie Springer-Verlag, Berlin, it is stated without reference that glycerol is derived in *Saccharomyces cerevisiae* from D-GP. However, in a 1949 journal, author Baranowski made the opposite assertion, stating that glycerol is known to originate from L-GP in both rabbit tissue and yeast. Baranowski, J. Biol Chem 180:535, 1949. Baranowski referenced a 1937 paper by Meyerhof et al. (Erg. Physiol. 39:10–77, 1937) as the source for yeast information; the 1937 paper states that L-α-GP is the only isomer that occurs naturally in yeast and that glycerol is derived from α-GP in yeast. The ambiguity was resolved in a 1968 report by Gancedo et al, which reported experiments showing that "the [S. cerevisiae] α-GPase is specific for the L form, the efficiency of α-GPase on D-GP being ⅟₃₀ of that on L-GP." Gancedo, et al., Eur. J. Biochem. 5: 165–172, 1968. Furthermore, Wassef et al. Can. J. Biochem. 48:69–73, 1970 asserted that the only known naturally occurring isomer of GP is the L form, both in bacteria and higher organisms.

The literature also contains misprints which reflect the lack of knowledge about the stereoisomeric glycerol phosphatases, and accordingly should be rectified. For example, in Enzyme Nomenclature 1992, Academic Press, San Diego, Calif., 1992, glycerol-1-phosphatase (EC 3.1.3.21), the D form is listed as preferentially hydrolyzed by *Dunaliella salina*, citing as reference a paper by Sussman et al. (Biochim. Biophys. Acta 661: 199–204, 1981). However, the referenced paper states that ". . . it is evident that the enzyme prefers the L form which is hydrolyzed more rapidly than the D form at limiting substrate concentrations."

In addition, Chemical Abstracts, Abstract 109:88569v states that ". . . Glycerol-3-phosphatase (EC 3.1.3.2.1) [sic] was studied by following the release of radioactive glycerol from D-(U-$^{14}$C)glycerol-3-phosphate in *D. tertiolecta* enzyme extracts . . ." However, in the reference cited in Abstract 109:88569v, the "D" is replaced by "L". Belmans, et al., Arch. Microbiol. 150: 109–112, 1988.

The present invention presents the first experimental evidence of a specific D-GPase. The *B. licheniformis* enzyme was found to catalyze the dephosphorylation of D-GP to produce glycerol and inorganic phosphate. It does not accept L-GP, β-GP, dihydroxyacetone phosphate, D-glyceraldehyde phosphate, glucose-6-phosphate, D-3-phosphoglyceric acid, or p-nitrophenyl phosphate as a substrate. The enzyme was found in the cytosolic fraction of crude cell extracts, and remains soluble in aqueous solution in the absence of detergents. It retains activity in dilute aqueous solution for at least three months at 4° C.

The presence of inorganic phosphate in assays of *B. licheniformis* extracts did not acutely inhibit D-GPase activity, nor did it harm glycerol production in anaerobic *B. licheniformis* glucose fermentations. The $K_m$ of D-GPase for D-GP was found to be about 4.3 mM. This value is low enough to be consistent with physiological hydrolysis of D-GP. For example, the $K_m$ values of β-galactosidase, threonine deaminase, and carbonic anhydrase are about 4, 5, and 8 mM, for lactose, threonine, and carbon dioxide, respectively Stryer, L., Biochemistry, 3rd Ed., W. H. Freeman and Company, New York, 1988, p. 190. The above observations are all consistent with the hypothesis that D-GPase dephosphorylates D-GP in the cytosol of *B. licheniformis* and that it catalyzes the final step in glycerol formation in anaerobic *B. licheniformis* glucose fermentations. However, it is currently not known whether D-GP occurs naturally in *B. licheniformis*.

If the glycerol pathway does proceed through D-GP, it would permit glycerol synthesis without the necessity of disturbing the L-GP pool, which is used for phospholipid synthesis. This is a similar strategy to the one used by organisms like *Aspergillus niger*, in which dihydroxyacetone is the metabolite that precedes glycerol. Legisa, et al., Enzyme Microb. Technol. 8: 607–609 (1986). Here, however, the two GP stereoisomers would have distinct roles as metabolic intermediates in the cell, the D form catabolic and the L form anabolic.

The possibility remains that the *B. licheniformis* D-GPase catalyzes a reaction in vivo with a substrate not tested. For example, phosphatidylglycerol (PG) is a phosphate ester of D-GP, Ratledge and Wilkinson (eds.), Microbial Lipids, Vol. 1, Academic Press Ltd., p. 35, 1988, and perhaps the enzyme catalyzes the breakdown of PG or a related compound. However, the D-GPase was found in the cytosol, making it an unlikely candidate for involvement in reactions with membrane components. The enzyme appears to be very specific for D-GP, not accepting the very similar D-glyceraldehyde phosphate. Indeed, PG is less structurally similar to D-GP than D-glyceraldehyde phosphate, the phosphate of the D-GP moiety being part of a phosphodiester linkage rather than a simple phosphate group.

The novel D-GPase enzyme of the present invention can provide a new way to make L-α-glycerol-3-phosphate (L-GP), previously synthesized by starting with D-mannitol, as described in *Biochemical Preparations*, Vol. 2, John Wiley & Sons, Inc., Vol. 2:31–38, 1952. To make L-GP using D-GPase, a racemic mixture of glycerol phosphate (which mixture will contain both D- and L-α-glycerophosphate, and also some β-glycerol phosphate) is first chemically synthesized, using methods well-known to those skilled in the art. Upon treatment of the racemic mixture with D-GPase, D-GP in the mixture will be hydrolyzed to glycerol. In the final step, the desired product, L-GP, can readily be separated from β-glycerol phosphate and glycerol. Another more recent method of L-GP preparation, from Crans and Whitesides, J. Am. Chem. Soc. 107:7019-7027 (1985), uses glycerol kinase and glycerol, with ATP as the source of phosphate, and acetyl phosphate and acetate kinase as the ATP regeneration system, a method of greater complexity and cost than the method envisioned here.

Materials and Methods

Materials

"Ford's strain" of *Bacillus licheniformis* (ATCC 9789, deposited in 1945) was obtained from the American Type Culture Collection (Rockville, Md.) DL-GP (82% and 95%), L-GP (95%), and β-GP ($\leq 0.1$% L-GP) were obtained from Sigma (St. Louis, Mo.). Water in all solutions was treated with the MILLI-Q Water System (Millipore, Bedford, Mass.) prior to use.

Protein Assay

Protein was measured by the Bradford method using the Protein Assay Kit from Bio-Rad (Hercules, Calif.) with bovine serum albumin as the standard.

Enzyme Assays

GPase activity was measured by combining cell extract and the appropriate stereoisomer(s) (DL or L) of GP, incubating the mixture, terminating the reaction with acid, and determining the glycerol content by high-performance liquid chromatography (HPLC) analysis. Assay mixtures consisted of, in a total of 500 µl:25 mM $MgCl_2$; 25–50 mM PIPES [piperazine-N,N'-bis(2-ethanesulfonic acid)], pH 7.1; 25–100 mM substrate; and the required volume of cell extract. Incubations were carried out at 37° C. for 30–150 min in microcentrifuge tubes, then 72 µl of 20% trichloroacetic acid (TCA) was added (2.5% final) to each tube to stop the reaction. The samples were spun in a microcentrifuge to remove any precipitate, and the supernatants were filtered through Supor-200 0.2 µm membrane filters (Gelman Sciences, Ann Arbor, Mich.) and analyzed for glycerol by HPLC. Assays for dephosphorylation of other compounds were also analyzed by HPLC (for the dephosphorylated compound) and carried out in the same way as the assays with GP as substrate. Assays for p-nitrophenyl phosphate (PNPP) hydrolysis were the same as with GP as substrate but were carried out with 1.5 mM PNPP in microtiter plates, and absorbance at 420 nm was used to measure the extent of hydrolysis of PNPP. Calf intestinal alkaline phosphatase was used as a standard to ensure that PNPP could be hydrolyzed under the conditions of the assay.

Glycerol Measurement by HPLC

Glycerol in fermentation broths and assay mixtures was measured by HPLC. The mobile phase was 0.01N $H_2SO_4$, run at a flow rate of 0.6 ml/min through an Aminex HPX-87H organic acids column (Bio-Rad, Hercules, Calif.), which was maintained at 65° C. Samples were injected by a model AS-100 autosampler, and chromatograms were printed by a model 3392A integrator; the detector was a model 1770 differential refractometer (all from Bio-Rad).

Phosphate Determinations

Assays that were analyzed for inorganic phosphate instead of glycerol were carried out using the procedure of Marsh, Biochim. Biophys. Acta, 32:357–361, 1959, with 0 to 0.12 mM final $KH_2PO_4$ as standards. Blanks were identical assays except without substrate.

D-GPase Purification (i) Bacterial Culture

Ten liters of GYF medium (25 g/liter glucose; 5 g/liter yeast extract [Difco, Detroit, Mich.]; and 300 mM $K_2HPO_4$/$NaH_2PO_4$, pH 7.0) were inoculated with 2 ml of an overnight aerobic *B. licheniformis* culture. The fermentation was carried out in a plastic carboy with a closed lid and no agitation at 37° C. The pH of the culture was allowed to drop to 6.2, which occurred after 12 h. HPLC analysis was used to verify the production of glycerol.

(ii) Protoplast Formation

Whole cells were collected by centrifugation at 2,500×g for 15 min at 4° C., resuspended in wash buffer (10 mM PIPES, pH 7.1, and 1 mM phenylmethylsulfonyl fluoride, abbreviated "PMSF") and spun again. The washed cells were then resuspended in 300 ml of wash buffer which also included 1.5 mg/ml of lysozyme and 2000 units of DNase I. After 2 h at 37° C. with gentle shaking in an unbaffled 1-liter Erlenmeyer flask, protoplasts were collected by centrifugation 12,000×g for 20 min at 4° C., resuspended in wash buffer, and spun again for 15 min. The protoplasts were resuspended in an equal volume of 1 mM PMSF-25 mM PIPES, pH 7.1 and frozen at −20° C.

(iii) Sonication of Protoplasts

The frozen protoplast suspension was thawed and then sonicated (W-385 sonicator, Heat Systems-Ultrasonics, Inc., Farmingdale, N.Y.) with a microtip in 3-ml aliquots on ice for 5 min each at a 70% cycle with a one-second interval. The sonicant was spun in a microcentrifuge at top speed for 10 min and the supernatant was collected and designated crude cell extract (CCE).

(iv) Ultracentrifugation

The CCE was ultracentrifuged at 120,000×g for 1 h at 4° C., and the supernatant was collected and designated ultracentrifuged CCE (UC).

(v) Ammonium Sulfate Fractionation

Ammonium sulfate (313.5 mg per ml of uc, 50% saturation) was added over the course of 1 h to well-stirred UC at room temperature. The resulting precipitate was removed using a microcentrifuge at top speed for 5 min, and the supernatant was collected for dialysis.

(vi) Dialysis

The supernatant from the ammonium sulfate fractionation was dialyzed overnight at 4° C. against 150 volumes of 10 mM PIPES, pH 7.1, and 25 mM $MgCl_2$. The cutoff molecular weight of the Spectra/Por dialysis membrane (Spectrum Medical Industries, Inc., Los Angeles, Calif.) was 12 to 14 kDa. The small amount of resulting precipitate was removed from the dialysate by centrifugation and the supernatant was collected and designated dialysis-soluble extract (UC-50-DS).

(vii) Anion-Exchange Chromatography

Five milliliters of UC-50-DS were loaded onto a POROS Q column (4.6×100 mm) in a BioCAD system (PerSeptive; Cambridge, Mass.). The mobile phase was 50 mM Tris and 50 mM bis-Tris propane, pH 6.0, and was run through the system at a flow rate of 15 ml/min. A linear gradient of NaCl from 0 to 1M was run through the column over the course of 15 column volumes (0.6M/min). The final gradient concentration was maintained for an additional 10 column volumes. Thirty-nine 1-ml fractions were collected.

(viii) Gel Filtration Chromatography

One-tenth (100 µl) of the most active fraction from the Q column was loaded onto a Biosep SEC-S3000 column (Phenomenex, Torrance, Calif.) and run at a flow rate of 1.0 ml/min with a mobile phase of PBSA (10 mM $K_2HPO_4$/$KH_2PO_4$, pH 7.05, 140 mM NaCl, 0.02% sodium azide). Twenty 1-ml fractions were collected.

pH Profile Analysis

The assays for pH profile analysis were run with DL-GP (82%) at a final D-GP concentration of 25 mM in a total volume of 500 µl. Each assay also contained 100 µl of UC, $MgCl_2$ at 25 mM, and one of the following buffers at 100 mM: citric acid/potassium citrate at pH 4.4 or 5.3, PIPES at pH 6.2 or 7.1, Tris at pH 8.0 or 8.9.

Kinetic Measurements

Assays for measurement of the $K_m$ of D-GPase for D-GP contained, in a total volume of 500 µl:50 µl of an anion-exchange column fraction; 1 mM or 5 mM $MgCl_2$; 50 mM PIPES, pH 7.1; and DL-GP (95%) at final D-GP concentrations ranging from 0 mM to 7.5 mM.

Enzymatic Analysis of Glycerol

An assay mixture (after incubation and termination with TCA) was run on the HPLC, and four fractions were collected. One corresponded to the peak identified as glycerol (12.00–13.25 min retention time). Each fraction was adjusted to pH 7.1 by adding PIPES to a final concentration of 70 mM. A glycerol dehydrogenase assay was run with the glycerol peak, with the DL-GP peak, and with two fractions that did not correspond to any peak. This assay consisted of, in 1 ml total volume: 100 mM potassium carbonate buffer, pH 10.0; 30 mM ammonium sulfate, 0.05 units glycerol dehydrogenase (Sigma; St. Louis, Mo.); 400 µM NAD+; and 100 µl of HPLC fraction. Evolution of NADH was observed at 340 nm. Only the glycerol fraction, and not the others, gave a positive result (increase in absorbance at 340 nm over time). Biolyzer (Eastman Kodak; Rochester, N.Y.) triglyceride slides were also used to confirm the presence of glycerol. These slides detect triglycerides, GP, and glycerol. A slide was cut into four pieces, each of which was dabbed with one fraction. Only the fractions corresponding to GP and glycerol, and not the others, gave positive results (change to blue color).

EXAMPLES

Glycerol Production by B. licheniformis

An important initial step was to identify conditions under which B. licheniformis produces high levels of glycerol from glucose. Conditions that were investigated included temperature (30° C., 37° C., or 45° C.), initial glucose concentration (10 g/liter or 25 g/liter), yeast extract concentration (1 g/liter or 5 g/liter), and buffer (150 mM PIPES or 300 mM $K_2HPO_4$/$NaH_2PO_4$, each at pH 7.1). All fermentations were anaerobic and were not sparged or agitated.

All 24 combinations of the above conditions were tested. After 35 h, glycerol was detected in all of the fermentations at concentrations ranging from 0.7 g/liter to 2.9 g/liter. The results are presented in Table 1. The inventors selected 37° C. and GYF medium (25 g/liter glucose, 5 g/liter yeast extract and 300 mM phosphate buffer, pH 7.1) as the standard conditions in which to grow cells to be assayed for GPase. The fermentation with this set of conditions gave slightly less glycerol (2.48 g/L) than two PIPES-buffered fermentations but proved best among phosphate-buffered fermentations. The inventors reasoned that it would be desirable to grow cells in a phosphate-rich medium so that nonspecific phosphatases would be repressed and not interfere with GPase assays.

TABLE 1

Final glycerol concentrations in B. licheniformis fermentations.

| Conditions* | Final glycerol, g/liter |
|---|---|
| HgyP | 2.94 |
| HGyP | 2.50 |
| MGYF | 2.48 |
| MgyP | 2.45 |
| MGyP | 2.43 |
| MGyF | 2.37 |
| HGYF | 2.27 |
| HGYP | 2.00 |
| MgYP | 1.95 |
| HgYP | 1.94 |
| LGYF | 1.87 |
| LgyF | 1.75 |
| HGyF | 1.54 |
| LGyF | 1.47 |
| LgYF | 1.38 |
| MGYP | 1.30 |
| HgyF | 1.24 |
| MgyF | 1.23 |
| MgYF | 1.12 |
| LGYP | 1.04 |
| LgYP | 0.97 |
| LGyP | 0.91 |
| LgyP | 0.89 |
| HgYF | 0.72 |

*The four characters used to describe fermentation conditions are in the order: temperature, [glucose], [yeast extract], buffer. Abbreviations used: (L,M,H), (30° C., 37° C., 45° C.); (g,G), (10,25) g/liter glucose; (y,Y), (1,5) g/liter yeast extract; to give, (P,F), (PIPES, phosphate).

Purification of D-GPase

Table 2 outlines the steps taken to purify the enzyme, B. licheniformis D-GPase; the purification steps are described in detail above. Crude cell extract was ultracentrifuged, fractionated with ammonium sulfate, dialyzed, and further purified by anion-exchange and gel-filtration chromatography. Gel-filtration analysis indicated that active D-GPase has an approximate molecular weight of 25 kDa. The enzyme remains soluble and active for at least 3 months at 4° C. in dialyzed extracts and anion-exchange column fractions. Overall, a purification of 85.4-fold with a recovery of 0.08% resulted in a specific activity of 37.48 units (µmol glycerol released per min) per mg protein. The seemingly low number of D-GPase activity from the column fraction (37.48 in Table 2) is probably due to loss in enzymatic activity due to level of dilutions. Specific activities of 93 and 130 were obtained in subsequent purifications.

TABLE 2

Purification of B. licheniformis D-GPase.

| Purification step | Total protein (mg) | Total activity (U) | Sp. act. (U/mg) | Recovery (%) | Purification (fold) |
|---|---|---|---|---|---|
| Crude cell extract | 228.2 | 100.18 | 0.439 | 100 | 1 |
| Ultracentrifugation | 19.13 | 26.55 | 1.388 | 26.5 | 3.2 |
| $(NH_4)_2SO_4$ prep/dialysis | 7.99 | 18.69 | 2.339 | 18.7 | 5.3 |
| Anion exchange column | 0.142 | 2.14 | 15.14 | 2.14 | 34.5 |
| Gel filtration column | 0.0022 | 0.0825 | 37.48 | 0.0823 | 85.4 |

Specificity of D-GPase

Upon the finding that a GPase was present in B. licheniformis extracts, the inventors sought to determine which GP isomers are dephosphorylated by the enzyme and whether some other common phosphorylated metabolites can also be accepted as substrates. Because the initial assays were conducted with DL-GP, which also contained a small amount of β-GP, the specificity of the enzyme was unclear. HPLC chromatograms of reactions were run with crude cell extract and either DL-GP, L-GP, or β-GP. Table 3 shows the corresponding activity of the *B. licheniformis* GPase with each substrate. The enzyme has a much higher activity with DL-GP than with L-GP, indicating that it is specific for the D form. The low activity with pure β-GP rules out the possibility that the activity seen in assays with DL-GP is due to the presence of β-GP as an impurity in the DL-GP preparation. Also tested were D-glyceraldehyde phosphate, dihydroxyacetone phosphate, glucose-6-phosphate, and D-3-phosphoglyceric acid, which are structurally very similar to D-GP, and also p-nitrophenyl phosphate, and little or no hydrolysis of any of these substrates was detected.

TABLE 3

Specificity of *B. licheniformis* D-GPase.

| Substrate | Relative activity with NO (%) |
| --- | --- |
| DL-α-glycerophosphate | 1.00 |
| L-α-glycerophosphate | 0.0250 ± 0.0066 |
| β-glycerophosphate | 0.0112 ± 0.0024 |

To ensure that the product being observed in the assays was truly glycerol, the HPLC fraction that contained the "glycerol" peak and three other fractions were collected. Glycerol dehydrogenase assays and tests with triglyceride indicator slides confirmed that glycerol was indeed a product of the reaction.

Characterization of D-GPase

Figure 1B:
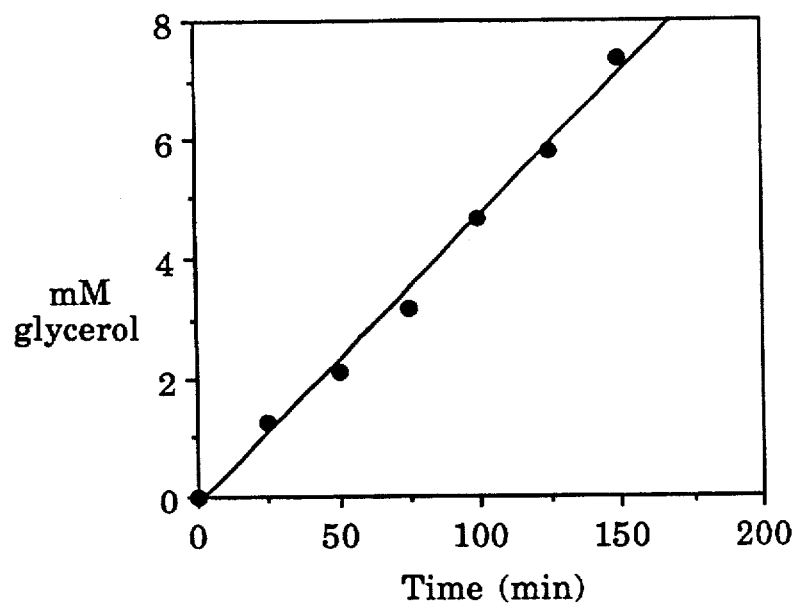
Figure 2:
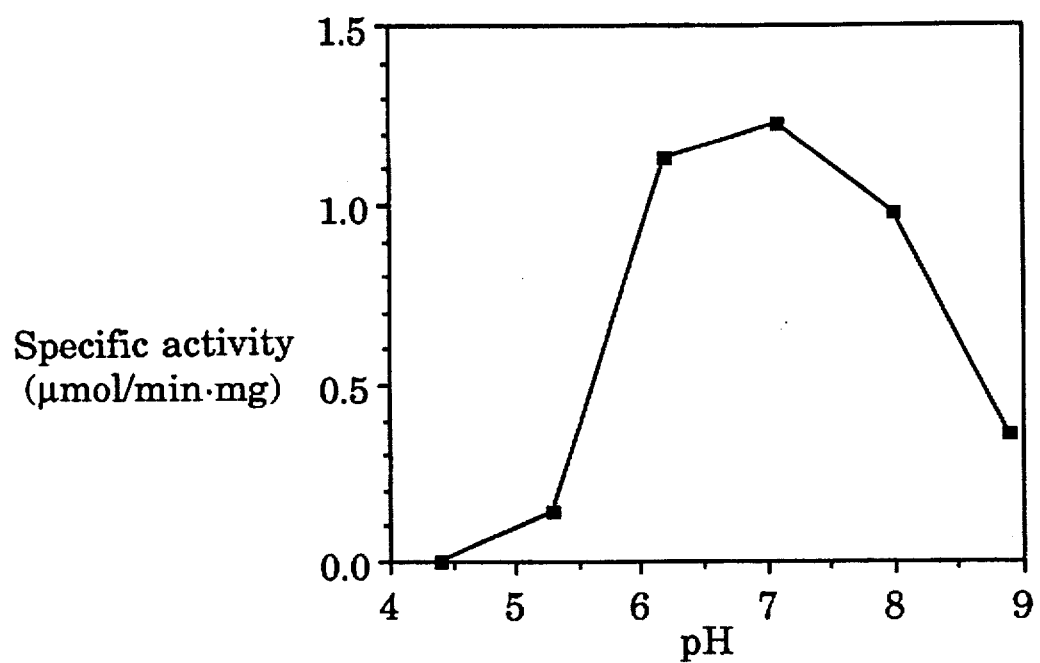
FIG. 2 is a graph illustrating the effect of pH on D-GPase activity.

The linearity of the D-GPase assay was tested by conducting assays at various levels of crude cell extract and with various incubation times. The results are presented in FIGS. 1a and 1b. "CCE" in FIG. 1a refers to crude cell extract as described in Materials and Methods. The amount of glycerol that accumulated in the assay mixture was found to be linear with time until at least 150 min of incubation. This amount was also reasonably linear with the volume of crude cell extract used, up to 40% of the total assay mixture. The effect of pH on D-GPase activity was also determined to ensure that the pH of our assay was near the optimum. The highest activity among those tested between pH 4.4–8.9 was at pH 7.1, as shown in FIG. 2.

L-GPases reported in the literature require divalent magnesium. Therefore, the inventors tested the effects of addition of the chlorides of three divalent cations: magnesium, manganese, and calcium (25 mM each). The results, presented in Table 4, show that magnesium, and to a lesser extent manganese, can fulfill the metal-ion requirement of D-GPase, and that while calcium cannot be used by the enzyme, it does not inhibit D-GPase activity.

TABLE 4

Effectiveness of divalent cations as cofactors.

| Cation added | Relative activity |
| --- | --- |
| $Mg^{2+}$ | 1.00 |
| $Mn^{2+}$ | 0.53 |
| $Ca^{2+}$ | 0.08 |
| None | 0.09 |

Phosphatases commonly yield either ATP or inorganic phosphate as a product. The inventors determined which one of them was a product of D-GPase. When 9 mM ADP was added to the assays, neither the specificity nor the level of activity of D-GPase was affected. In addition, GPase assays that were quantified by measurement of inorganic phosphate rather than glycerol showed the liberation of phosphate above background levels in the presence of D-GP. This indicates that inorganic phosphate, and not ATP, is a product of the D-GPase reaction. Because *B. licheniformis* can produce glycerol in a fermentation containing plentiful phosphate, the inventors determined whether phosphate had a significant effect on the rate of hydrolysis of D-GP in vitro. In the presence of 25 mM inorganic phosphate, the enzyme still retained 75% of its activity. This is consistent with the possibility that the enzyme catalyzes the terminal reaction in the *B. licheniformis* pathway to glycerol.

Figure 3:
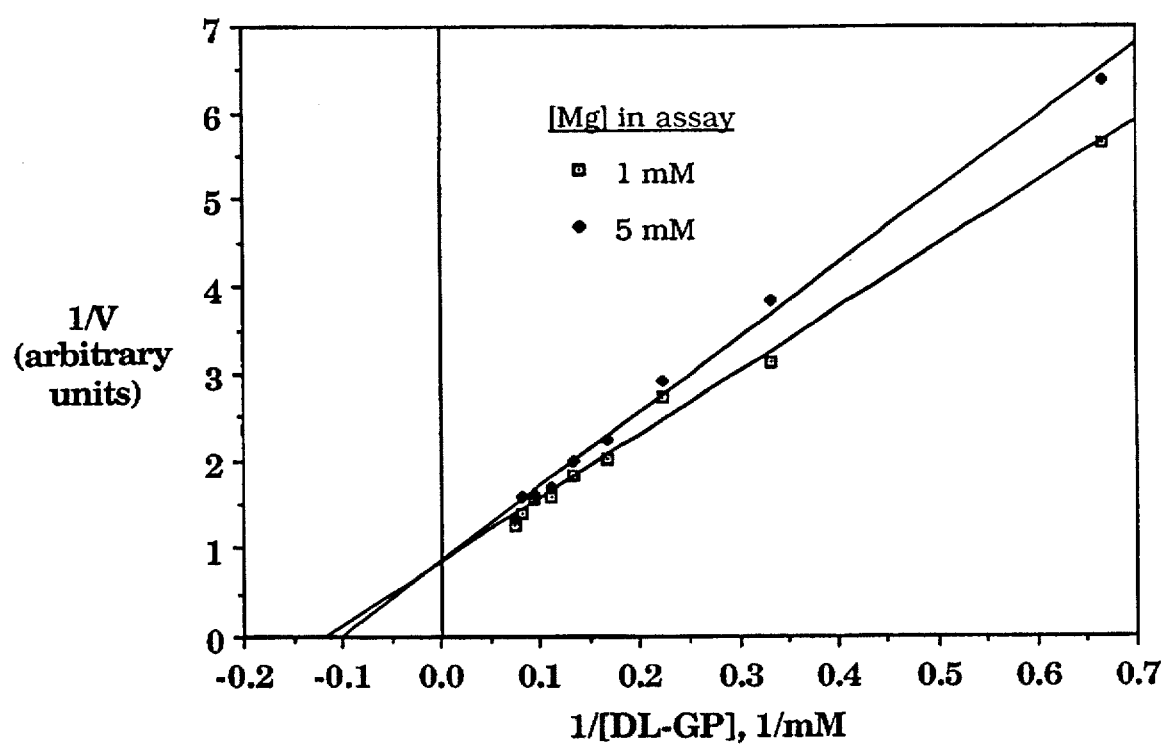
FIG. 3 is a graph representing the results of determining the Michaelis constant of D-GPase.

To further investigate whether the enzyme D-GPase uses D-GP as its physiological substrate, the inventors determined its Michaelis constant, $K_m$. The $K_m$ value was determined by assaying the activity of a partially purified fraction in the presence of 1 mM or 5 mM $Mg^{2+}$. A Lineweaver-Burk plot, shown as FIG. 3, of the data was made, and the $K_m$ for DL-GP was taken for each $Mg^{2+}$ concentration as the negative reciprocal of the x-intercept of a least-squares fit of the data. Assuming the DL-GP used was an equal mixture of the two stereoisomers, the $K_m$ for D-GP was estimated by dividing the $K_m$ for DL-GP by two.

Sequence Analysis of D-GPase

The inventors discovered that the purified D-GPase of the present invention has an approximate molecular weight of 25 kDa. Now that the enzyme has been purified, the N-terminal protein sequence will be recovered so that the amino acid sequence of the protein can be determined by commonly used methods of molecular biology well-known to those of skill in the art. In general, the following steps are necessary to sequence a purified protein: (1) cleavage of all disulfide bonds; (2) determination of the terminal amino acid residues; (3) specific cleavage of the polypeptide chain into small fragments in at least two different ways; (4) independent separation and sequence determination (such as by the Edman degradation) of peptides produced by the different cleavage methods; and (5) reassembly of the individual peptides with appropriate overlaps to determine the overall amino acid sequence.

Once the amino acid sequence of D-GPase is determined, the enzyme can be readily synthesized by automated solid phase methods well known to those who are skilled in the art, which methods are set forth in the textbooks "*Principles of Peptide Synthesis*", Springer-Verlag, 1984; "*Solid Phase Peptide Synthesis*", J. M. Stewart and J. D. Young, Pierce Chemical Company, Rockford, Ill., 1984 (2nd ed.); G. Barany and R. B. Merrifield, "*The Peptides*", Ch. 1, pp. 1–285, Academic Press.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) can be removed sequentially or concurrently, to afford the final polypeptide.

RECOMBINANT DNA TECHNOLOGY

Once the amino acid sequence of the novel enzyme D-GPase is known, it is within the skill of the art to identify and isolate the gene coding for the enzyme, and to prepare it by means of recombinant DNA technology, as an alternative to isolating the enzyme from *B. licheniformis* or preparing it by means of automated solid phase peptide synthesis.

In order to prepare D-GPase by means of recombinant DNA technology, a gene for the peptide must first be created. For peptides of the length of D-GPase, it is readily possible to artificially synthesize DNA of proper sequence to encode the peptide. Oligonucleotide synthesis can be used to create DNA segments which can be joined for a DNA coding sequence for the peptide.

Alternatively, the gene for the peptide can be isolated from a cell's total DNA by screening a library of that cell's DNA. The DNA library is screened by use of probes, synthetic radiolabelled nucleic acid sequences which can be used to detect and isolate complementary base sequences by hybridization. Knowing the amino acid sequences, probes for the gene can be designed based on the fact that each amino acid of the peptide is specified by a specific codon, or sequential grouping of three nucleotides. The possible nucleotides are adenine (A), guanine (G), cytosine (C), and thymine (T). The codons which are specific for each of the twenty amino acids found in proteins or peptides, and the codons which signal termination of protein synthesis, are well known; although there is more than one codon for certain amino acids, no codon specifies more than one amino acid. Because some amino acids have several possible codons and it is not initially known which of the possible codons will actually code for an amino acid, a set of probes can be designed that covers all possible codons for each amino acid comprising the peptide; such a set of probes is known as a "fully degenerate" set of probes.

The library to be screened can be a genomic library (gDNA), which contains a set of all the DNA sequences found in an organism's cells, or a complementary DNA (cDNA) library, which is much smaller and less complex than a gDNA library, as is used frequently when the tissue source for a given gene is known.

Enzyme effectiveness, whether isolated from *B. licheniformis* or produced by means of automated solid phase peptide synthesis or recombinant DNA technology, can be evaluated by means of the procedures described above.

When the gene for the peptide has been made, it can be used to form a genetic construct by inserting it into a plasmid or vector having suitable flanking regulatory sequences (e.g. promoter) for a desired host. The recombinant plasmid or vector with the inserted gene—the cloned gene—is then introduced ("transformed" or "transfected"), into a host cell. The vector or plasmid host cell at that point is "transformed" or "transfected". The vector or plasmid is the carrier which brings the DNA or gene of interest into the host cell, and allows the DNA to replicate as the host cell grows and replicates, eventually causing the host cell to express or produce the peptide.

To express a *B. licheniformis* gene sequence in a host, it is required that the DNA sequence containing the D-GPase coding sequence be combined with a promoter located 5' to the DNA coding sequence and a 3' termination sequence. Commonly used methods of molecular biology well-known to those of skill in the art may be used to manipulate such DNA sequences. By "gene construct" we mean any of a variety of ways of combining the protein-encoding sequence with promoter and termination sequences in a manner that operably connects the promoter and termination sequences with the protein-encoding sequence. Typically, the promoter sequence will be 5' or "upstream" of the protein-encoding sequence, while the termination sequence will be 3' or "downstream" of the protein-encoding sequence.

For example, the gene encoding D-GPase can be transformed (together with promoter and termination sequences) into a host (such as a bacterium) that produces D-GP as an intermediary metabolite. When cultured, the transformed host would then be able to form glycerol from sugars, because the expressed D-GPase would specifically dephosphorylate D-GP.

We claim:

1. A composition of matter comprising a glycerol phosphatase from *Bacillus licheniformis*, isolated from a host, which has a stereo-specific preference for substrate of D-α-glycerophosphate over L-α-glycerophosphate.

2. A composition of matter comprising an extract from a culture of *Bacillus licheniformis*, the extract containing enzymatic glycerol phosphatase activity specific to D-α-glycerophosphate.

3. A DNA sequence isolated from a host comprising DNA encoding a D-α-glycerophosphatase from *Bacillus licheniformis*.

4. A isolated and purified sample of DNA, the DNA comprising a DNA sequence coding for D-α-glycerophosphatase from *Bacillus licheniformis*.

5. A vector containing the DNA sequence of claim 4.

6. A D-α-glycerophosphate-producing microbial host transformed by the vector of claim 5.

7. A genetic construct in a heterologous host capable of producing D-α-glycerophosphatase from *Bacillus licheniformis*.

8. A method for producing glycerol from D-α-glycerophosphate comprising the steps of a) providing a quantity of D-α-glycerophosphate;

b) exposing the D-α-glycerophosphate to a D-α-glycerophosphatase from *Bacillus licheniformis* under conditions favorable to enzymatic action; and c) recovering glycerol.

9. A method as claimed in claim 8 wherein step a) the D-α-glycerophosphate is part of a racemic mixture of D- and L-α-glycerophosphate.

10. A method as claimed in claim 8 wherein step b) is performed in a microbial host.

11. A method for separating L-α-glycerophosphate from DL-α-glycerophosphate comprising the steps of a) making a racemic mixture of DL-α-glycerophosphate;

b) exposing the racemic mixture to the enzymatic activity of a D-α-glycerophosphatase from *Bacillus licheniformis* to convert the D-α-glycerophosphate to glycerol; and c) separating the glycerol from the L-α-glycerophosphate.

* * * * *

UNITED STATES PATENT AND TRADEMARK OFFICE
CERTIFICATE OF CORRECTION

PATENT NO. : 5,733,749
DATED      : March 31, 1998
INVENTOR(S): Douglas C. Cameron; Frank A. Skraly It is certified that error appears in the above-identified patent and that said Letters Patent is hereby corrected as shown below:

Column 1, line 3, insert the following information:

--This invention was made with United States government support awarded by the following agencies: EPA Grant # R819688. The United States has certain rights in this invention.--

Signed and Sealed this

Seventh Day of July, 1998

Attest:

BRUCE LEHMAN

Attesting Officer

Commissioner of Patents and Trademarks